US006965057B2

(12) United States Patent
Beech, Jr. et al.

(10) Patent No.: US 6,965,057 B2
(45) Date of Patent: Nov. 15, 2005

(54) OXYGENATE TO OLEFIN PROCESS

(75) Inventors: James H. Beech, Jr., Kingwood, TX (US); Cor F. Van Egmond, Pasadena, TX (US); Teng Xu, Houston, TX (US); James R. Lattner, Seabrook, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 51 days.

(21) Appl. No.: 10/807,818

(22) Filed: Mar. 24, 2004

(65) Prior Publication Data

US 2005/0215840 A1 Sep. 29, 2005

(51) Int. Cl.⁷ .......................... C07C 1/207; B01J 20/34
(52) U.S. Cl. ..................... 585/640; 585/638; 585/639; 502/38; 502/50
(58) Field of Search ................ 585/640, 639, 585/638; 502/38, 50

(56) References Cited

U.S. PATENT DOCUMENTS

| | | | |
|---|---|---|---|
| 3,494,858 A | 2/1970 | Luckenbach | 208/164 |
| 3,844,973 A | 10/1974 | Stine et al. | 252/417 |
| 3,923,686 A | 12/1975 | Stine et al. | 252/417 |
| 4,071,573 A | 1/1978 | Owen et al. | 260/688 R |
| 4,176,083 A | 11/1979 | McGovern et al. | 252/411 R |
| 4,206,174 A | 6/1980 | Heffley et al. | 422/144 |
| 4,405,445 A | 9/1983 | Kovach et al. | 208/120 |
| 4,744,883 A | 5/1988 | Hettinger, Jr. | 208/108 |
| 6,482,999 B2 | 11/2002 | Fung et al. | 585/640 |
| 2002/0013505 A1 | 1/2002 | Fung et al. | 585/640 |
| 2002/0094313 A1 | 7/2002 | Lu et al. | 422/216 |

OTHER PUBLICATIONS

Lu, W., et al, *Study on Rapid Stripping for FCC Regenerated Catalyst*, Petroleum Processing and Petrochemicals vol. 33/9, pp. 9-12 (2002) (Abstract).

Thomson Derwent Abstract for CN 1270853, Oct. 25, 2000 entitled "Stripping Method and Equipment for Catalytic Conversation Catalyst-Regenerating".

*Primary Examiner*—Thuan D. Dang

(57) ABSTRACT

The invention relates to a process for converting an oxygenate feedstock into an olefin product stream comprising (a) contacting an oxygenate feedstock with a molecular sieve catalyst in a reactor under conditions effective to convert the feedstock into an olefin product stream and to form carbonaceous deposits on the catalyst; (b) contacting at least a portion of the catalyst having said carbonaceous deposits with an oxygen containing gas under conditions effective to obtain a regenerated catalyst having a reduced carbonaceous deposit level and having an increased molecular oxygen content; (c) removing at least 60% by volume of said molecular oxygen from the regenerated catalyst based upon the total volume of molecular oxygen; (d) returning said regenerated catalyst to said reactor; and (e) repeating steps (a)–(d).

18 Claims, 2 Drawing Sheets

US 6,965,057 B2

OXYGENATE TO OLEFIN PROCESS

FIELD OF THE INVENTION

This invention relates to a process for converting oxygenates to olefins. In particular, the invention is an improved oxygenates-to-olefins process wherein the amount of oxygen molecules entrained in regenerated catalyst is reduced, thereby enhancing at least the activity and selectivity of the regenerated catalyst used in the oxygenates-to-olefins reaction.

BACKGROUND OF THE INVENTION

Light olefins such as ethylene, propylene, butylene and mixtures thereof, serve as feeds for the production of numerous important chemicals and polymers. A common method for producing light olefins is by cracking of petroleum feeds. However, because of the limited supply of competitive petroleum feeds, the opportunities to produce low-cost light olefins from petroleum feeds are limited. Efforts to develop light olefin production technologies based on alternative feeds have increased. For example, oxygenates such as alcohols, in particular methanol and ethanol, dimethyl ether, methyl ethyl ether, dimethyl carbonate and methyl formate are being considered as alternative feeds for the production of light olefins. These oxygenates-to-olefins processes typically use molecular sieve catalysts to promote the conversion of oxygenates to olefins. However, it has been found that during this reaction, carbonaceous material such as coke is deposited on or within the molecular sieve catalysts. Over-accumulation of this coke interferes with the catalyst's ability to promote the oxygenates-to-olefins reaction. Accordingly, the oxygenates-to-olefins process typically includes a step for regenerating the catalyst, which at least partially removes the coke from the catalyst by combustion in the presence of oxygen. The regenerated catalyst may then be reused in the oxygenates-to-olefins reaction.

It has been found that as a result of this regeneration step, oxygen molecules become entrained within the pores of the catalyst or interstitially between the catalyst particles themselves. It has also been found that over-abundance of these oxygen molecules reduce the activity and selectivity of the molecular sieve during the oxygenates-to-olefins reaction. It is therefore desirable to reduce the amount of entrained oxygen molecules present in regenerated catalyst prior to introduction of the regenerated catalyst into the oxygenates-to-olefins reactor. This invention satisfies this need.

SUMMARY OF THE INVENTION

The invention is a process for converting an oxygenate feedstock into an olefin product stream comprising (a) contacting an oxygenate feedstock with a molecular sieve catalyst in a reactor under conditions effective to convert the feedstock into an olefin product stream and to form carbonaceous deposits on the catalyst; (b) contacting at least a portion of the catalyst having said carbonaceous deposits with an oxygen containing gas under conditions effective to obtain a regenerated catalyst having a reduced carbonaceous deposit level and having an increased molecular oxygen content; (c) removing at least 60% by volume of said molecular oxygen from the regenerated catalyst based upon the total volume of molecular oxygen; (d) returning said regenerated catalyst to said reactor; and (e) repeating steps (a)–(d).

DETAILED DESCRIPTION OF THE INVENTION

Figure 1:
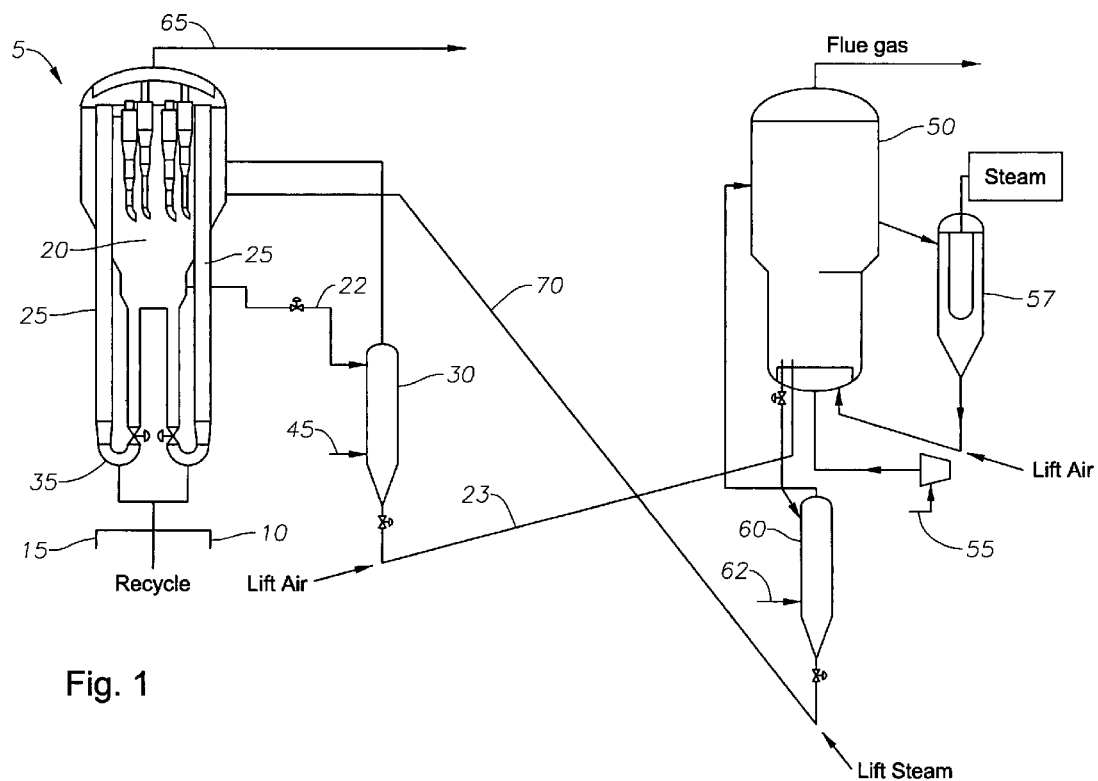
FIG. 1 is a diagram showing a process for converting an oxygenate feedstock into an olefin product stream in accordance with an embodiment of this invention, wherein at least a portion of the molecular oxygen entrained in the regenerated catalyst is removed prior to returning the regenerated catalyst to the reactor.

The presence of molecular oxygen during an oxygenates-to-olefins reaction has been found to significantly reduce the activity and selectivity of molecular sieve catalysts typically used to promote such reactions. Molecular oxygen can become entrained within the catalyst, either interstitially or within the catalyst pores, during regeneration of the catalyst. As used herein, interstitial molecular oxygen means molecular oxygen entrained between the molecular sieve particles, and pore contained molecular oxygen means molecular oxygen entrained within the catalyst pore volume. This invention provides a method for enhancing the performance of an oxygenates-to-olefins catalytic reaction by reducing the amount of molecular oxygen introduced into the reactor with the regenerated catalyst. In accordance with this invention, at least a portion of the interstitial and pore contained molecular oxygen is displaced with an inert gas before the regenerated catalyst enters the reactor.

The oxygenates-to-olefins reaction comprises contacting an appropriate feedstock with an appropriate molecular sieve catalyst at effective process conditions, i.e., an effective temperature, pressure, WHSV (Weight Hourly Space Velocity) and, optionally, an effective amount of diluent, so as to produce the desired olefins. The feedstock may be contacted in vapor phase, liquid phase, or a mixed vapor/liquid phase. Different conversion rates and selectivities of feedstock-to-product may result depending upon the catalyst, the reaction conditions, and the phase selected (i.e. vapor, liquid or vapor/liquid).

The oxygenates-to-olefins reaction may be conducted in a variety of reactors, which can be selected by one of ordinary skill in the art. For example, hybrid reactors that have a dense bed or fixed bed zones and/or fast fluidized bed reaction zones coupled together, circulating fluidized bed reactors, riser reactors, and the like may be used. Suitable conventional reactor types have been described in U.S. Pat. No. 4,076,796, U.S. Pat. No. 6,287,522, and Fluidization Engineering, D. Kunii and O. Levenspiel, Robert E. Krieger Publishing Company, New York, N.Y. 1977, which are all herein fully incorporated by reference.

Substantially any small or medium pore molecular sieve catalyst and equivalents thereof may be used in the oxygenates-to-olefins reaction. As used herein, a small pore molecular sieve is defined as a catalyst with pores having a diameter of less than about 5.0 Angstroms. A medium pore molecular sieve is defined as a catalyst with pores having a diameter in the range of from about 5 to 10 Angstroms.

A particular group of suitable molecular sieves that can be used in the oxygenates-to-olefins reaction are commonly known as zeolites. Structural types of small pore zeolites that are suitable for the oxygenates-to-olefins reaction include, but are not limited to AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, and THO and substituted examples of these structural types, as described in W. M. Meier and D. H. Olsen, Atlas of Zeolite Structural Types (Butterworth Heineman—3rd ed. 1997), incorporated herein by reference. Preferred zeolite catalysts include, but are not limited to, ZSM-5, ZSM-34, erionite and chabazite.

Silicoaluminophosphates (SAPOs) are another group of molecular sieve catalysts that are useful in the oxygenates-to-olefins reaction. SAPOs have a three-dimensional microporous crystal framework of $PO_2^+$, $AlO_2^-$, and $SiO_2$ tetrahedral units. Suitable SAPOs for use in the oxygenates-to-olefins reaction include, but are not limited to SAPO-34, SAPO-17 and SAPO-18. SAPOs having added substituents may also be useful in the oxygenates-to-olefins reaction. These substituted SAPOs form a class of molecular sieves known as MeAPSOs. Such substituents may include, but are not limited to nickel, cobalt, strontium, barium and calcium.

Structural types of medium pore molecular sieves useful in the oxygenates-to-olefins reaction include, but are not limited to MFI, MEL, MTW, EUO, MTT, HEU, FER, AFO, AEL, TON, and substituted examples of these structural types, as described in the *Atlas of Zeolite Types*, previously incorporated herein by reference.

The feedstock for the oxygenates-to-olefins process employs an organic starting material preferably comprising "oxygenates." An oxygenate is an organic compound that contains at least one oxygen atom. Preferably, the oxygenate feedstock comprises one or more alcohols, more preferably, aliphatic alcohols where the aliphatic moiety of the alcohol has from 1 to 20 carbon atoms, preferably from 1 to 10 carbon atoms, and more preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The feedstock may also contain one or more diluents to reduce the concentration of the feedstock. The diluent should be generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent may be used either in a liquid or a vapor form, or a combination thereof. The diluent is either added directly to a feedstock entering into the reactor or added directly into the reactor, or added with the molecular sieve catalyst composition. In an embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In an embodiment, other hydrocarbons are added to a feedstock either directly or indirectly, and include olefin(s), paraffin(s), aromatic(s) (see for example U.S. Pat. No. 4,677,242) or mixtures thereof, preferably propylene, butylene, pentylene, and other hydrocarbons having 4 or more carbon atoms, or mixtures thereof.

The temperature of the conversion process may vary over a wide range, depending at least in part on the selected catalyst. Although not limited to a particular temperature, preferably the process is conducted at temperatures in the range of about 200° C. to about 700° C., more preferably in the range of about 250° C. to about 600° C., and most preferably in the range of about 300° C. to about 500° C. Lower temperatures generally result in lower rates of reaction, and the formation of the desired light olefin products may become markedly slow. However, at higher temperatures, the process may not form an optimum amount of light olefin products, and the coking rate may become too high.

Light olefin products will form at a wide range of pressures, including but not limited to autogeneous pressures and pressures in the range of from about 0.1 kPa to about 100 MPa. A preferred pressure range is from about 6.9 kPa to about 34 MPa, most preferably in the range of from about 48 kPa to about 0.34 MPa. The foregoing pressures are exclusive of diluent, if any is present, and refer to the partial pressure of the feedstock as it relates to oxygenate compounds and/or mixtures thereof. Pressure outside of the stated ranges may be used and are not excluded from the scope of the invention. Lower and upper extremes of pressure may adversely affect selectivity, conversion, coking rate, and/or reaction rate. However, light olefins such as ethylene may still form.

A wide range of WHSV for the feedstock may be used. WHSV is defined as the weight feed (excluding diluent) per hour per weight of a total reaction volume of molecular sieve catalyst (excluding inerts and/or fillers). The WHSV generally should be in the range of from about 1 $hr^{-1}$ to about 5000 $hr^{-1}$, preferably in the range of from about 2 $hr^{-1}$ to about 3000 $hr^{-1}$, more preferably from about 5 $hr^{-1}$ to about 1500 $hr^{-1}$, and most preferably in the range of from about 10 $hr^{-1}$ to about 1000 $hr^{-1}$.

The reaction should be continued for a period of time sufficient to produce the desired olefin products. The reaction time may vary from tenths of seconds to a number of hours. The reaction time is largely determined by the reaction temperature, the pressure, the catalyst selected, the WHSV, the phase (liquid or vapor), and the selected process design characteristics.

Because carbonaceous deposits such as "coke" will form on the surface of or within the molecular sieve catalyst during the oxygenates-to-olefins reaction, the catalyst is typically regenerated by burning off at least a portion of the coke deposits. In an embodiment of this process, a portion of the coked molecular sieve catalyst composition is withdrawn from the oxygenates-to-olefins reactor and introduced to a regeneration system. The regeneration system comprises a regenerator where the coked catalyst composition is contacted with a regeneration medium, preferably a gas that contains oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (see U.S. Pat. No. 6,245,703, incorporated herein by reference), carbon monoxide and/or hydrogen.

Typical regeneration temperatures are in the range of from about 200° C. to about 1500° C., preferably from about 300° C. to about 1000° C., more preferably from about 450° C. to about 750° C., and most preferably from about 550° C. to 700° C. The regeneration pressure can be in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa).

The preferred residence time of the molecular sieve catalyst composition in the regenerator is in the range of from about one minute to several hours, most preferably about one minute to 100 minutes. The preferred volume of oxygen in the gas is in the range of from about 0.01 mole percent to about 5 mole percent based on the total volume of the gas.

In an embodiment, regeneration promoters are added to promote the regeneration of the molecular sieve. Regeneration promoters are typically metal containing compounds such as platinum, palladium and the like. These regeneration promoters may be added directly to the regenerator, or may be added indirectly, for example, with the coked catalyst composition.

The regeneration conditions are selected so that coke is burned from the coked catalyst composition to form a regenerated molecular sieve catalyst composition. In an embodiment, the regenerated molecular sieve catalyst has a coke level of less than about 2 wt. %, more preferably less than about 1 wt. % and more preferably less than about 0.5 wt. % based upon the total weight of the coked molecular sieve catalyst composition. However, the severity of regeneration can be controlled by one skilled in the art to provide a catalyst that retains some coking material, i.e. to obtain a partially regenerated catalyst, which has enhanced selectivation to light olefins during the oxygenates-to-olefins reaction. For example, U.S. Pat. No. 4,873,390 to Lewis et al., incorporated herein by reference, teaches the conversion of an alcohol feedstock to a product containing light olefins over a silicoaluminophosphate molecular sieve having pores with diameters of less than 5 Angstroms, wherein carbonaceous deposit material is formed on the catalyst. The catalyst is regenerated under conditions that form a partially regenerated catalyst having from 2 wt. % to 30 wt. % of the carbonaceous deposit material, with a preferred range between 4 wt. % and 20 wt. %. In another embodiment, the severity of coking is controlled by mixing regenerated catalyst with non-regenerated catalyst. For example, U.S. Pat. No. 6,023,005 to Lattner et al., incorporated herein by reference, discloses a method of producing ethylene and propylene by catalytic conversion of oxygenate in a fluidized bed reaction process which uses catalyst regeneration. The process maintains a portion of desired carbonaceous deposits on the catalyst by removing only a portion of the total reaction volume of coked molecular sieve catalyst and totally regenerating only that portion of catalyst, which is then mixed back with the unregenerated remainder of catalyst. The resulting catalyst mixture contains from about 2 wt. % to about 30 wt. % carbonaceous deposits.

It has been found that as a result of the regeneration step, oxygen molecules become entrained within or between the molecular sieve particles. These oxygen molecules have been found to be detrimental to the activity and selectivity of the oxygenates-to-olefins reaction. In accordance with this invention, the regenerated molecular sieve catalyst is treated to remove at least a portion of the molecular oxygen prior to introducing the regenerated catalyst into the reactor. As used in the specification and in the claims, the term "regenerated" can mean fully or partially regenerated molecular sieve catalyst. The treatment step to remove the molecular oxygen can be by any appropriate method, for example by stripping with an inert gas or steam. Preferably, at least 60% by volume of the oxygen molecules are removed, more preferably at least 65%, even more preferably at least 70%, even more preferably at least 75%, and most preferably at least 80% by volume. In an embodiment, the amount of molecular oxygen removed by the treatment step is between 65% to 95% by volume, preferably between 70% to 95%, more preferably between 75% to 95%, and most preferably between 80% to 95% by volume.

After the treatment step of removing at least a portion of the molecular oxygen, at least a portion of the treated regenerated catalyst is returned to the reactor. The treated regenerated catalyst can be added directly into a reaction zone, or added indirectly by pre-contacting the treated regenerated catalyst with the feedstock. The treated regenerated catalyst may also be returned to the reactor with a fresh molecular sieve catalyst composition.

A preferred embodiment of this invention is generally depicted in FIG. 1, where a methanol-to-olefins reaction is conducted in a dual riser reactor apparatus 5. The methanol feed 10 is at least partially vaporized in a preheater (not shown), and is optionally diluted with an inert gas and/or steam 15. The diluted feed is mixed with catalyst at the bottom of the riser reactor 35, and the mixture passed through reactor zone 25. The methanol-to-olefins reaction is exothermic, and accordingly, heat needs to be removed in order to maintain the preferred reaction temperature range in reactor zone 25. This heat removal can be accomplished using any suitable means, including but not limited to cooling the reactor with a catalyst cooler (not shown), feeding at least a portion of the methanol as a liquid, cooling the catalyst fed into the reactor, or any combination of these methods.

The effluent from reactor zone 25 contains reaction products, light olefins, coked catalysts, diluent(s), and unconverted feed. The reactor effluent flows into a disengaging zone 20, where the coked catalyst is separated from the gaseous materials by means of gravity and/or cyclone separators. The hot reactor product gases 65 can be cooled, the water byproduct condensed and collected, and the desired olefin product gases recovered for further processing (not shown). The coked catalyst settles to the lower portion of the disengaging zone 20, where a portion of the coked catalyst to be regenerated is removed through line 22, and sent to a hydrocarbon stripping vessel 30. Steam or other inert gas is used in the hydrocarbon stripping vessel 30 to recover adsorbed hydrocarbons from the catalyst, and the recovered hydrocarbons returned to the disengaging zone 20. The hydrocarbon stripped catalyst is transferred to the regenerator 50, for example through line 23.

In the regenerator 50, the stripped coked catalyst is contacted with a regeneration medium 55 at a temperature, pressure, and residence time selected to burn coke off of the catalyst to the desired level. The regeneration medium 55 is preferably a gas that contains oxygen. The burning off of coke is exothermic, and the temperature of the regeneration step can be maintained at a suitable level by any acceptable method, including but not limited to feeding the regeneration medium at a cooler temperature, cooling the catalyst using a catalyst cooler 57, or a combination of these methods.

Figure 2:
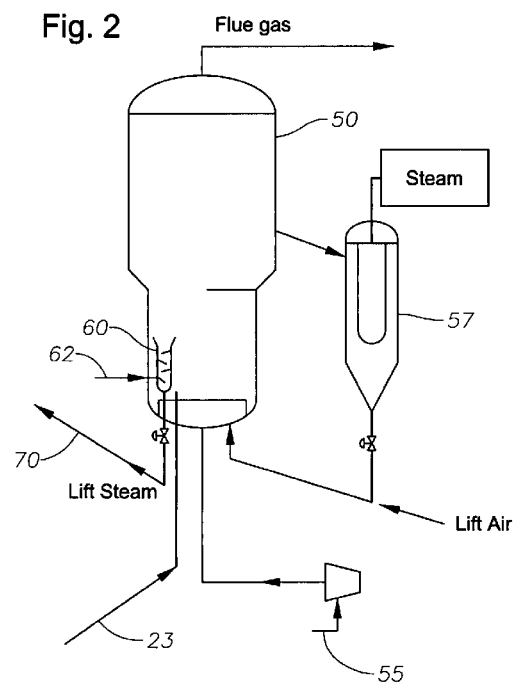
FIG. 2 is an embodiment of this invention wherein an oxygen stripper apparatus is located within the regenerator.
Figure 3:
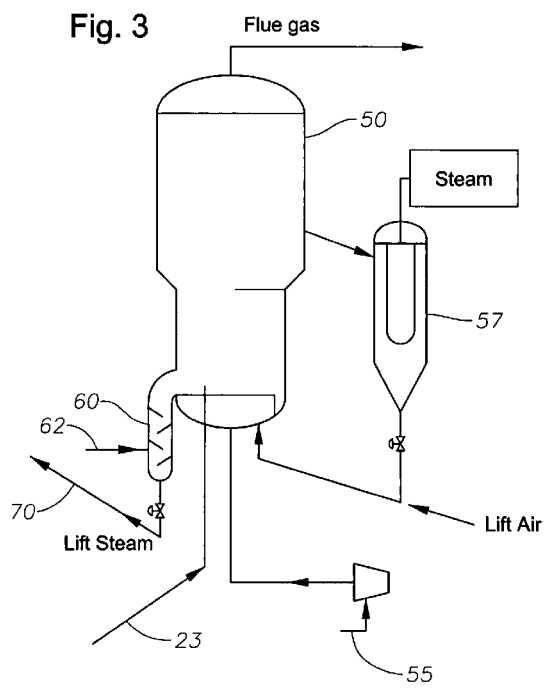
FIG. 3 is an embodiment of this invention wherein an oxygen stripper apparatus is affixed to the regenerator.

Referring again to FIG. 1, in accordance with this invention, after the catalyst is regenerated it is sent to a stripper 60, or other appropriate apparatus, where at least a portion of the oxygen molecules in the regenerated catalyst are removed. By way of further example, in an embodiment, the stripping apparatus 60 is located within regenerator 50, for example as shown in FIG. 2. In another embodiment, the stripping apparatus 60 is affixed to regenerator 50, for example as shown in FIG. 3. Stripping can be accomplished by purging the regenerated catalyst with an inert gas or steam 62 that does not contain oxygen. Preferably, at least 60% by volume of the oxygen molecules are removed, more preferably at least 65%, even more preferably at least 70%, even more preferably at least 75%, and most preferably at least 80% by volume. In an embodiment, the amount of molecular oxygen removed by the treatment step is between 65% to 95% by volume, preferably between 70% to 95%, more preferably between 75% to 95%, and most preferably between 80% to 95% by volume.

The stripped regenerated catalyst can then be sent back to the reactor 5, for example through line 70, for use in the oxygenates-to-olefins reaction. This process can repeat itself in a continuous or semi-continuous manner.

The present invention has been described in connection with its preferred embodiments. However persons skilled in the art will recognize that many modifications, alterations, and variations to the invention are possible without departing from the true scope of the invention. Accordingly, all such modifications, alterations, and variations shall be deemed to be included in this invention, as defined by the appended claims.

EXAMPLES

Table 1 lists the rates of entrained regenerator gas species for two cases: one case without molecular oxygen stripping of catalyst and a second case that includes molecular oxygen stripping of catalyst. The methanol feed rate is 744,399 kg/hr. The stripper is operated at a stripping steam rate of 4 kg stripping steam/metric ton catalyst flow rate. The catalyst flow rate is 194,060 kg/hr. Relevant catalyst densities are estimated to be 1490 kg/m³ particle, 2672 kg/m³ skeletal, and 561 kg/m³ standpipe flowing density. The stripper is estimated to be 75% efficient in displacing or removing the entrained interstitial and pore contained gases.

TABLE 1

ENTRAINED REGENERATOR GASES - NO STRIPPING

|  | Interstitial kg/hr | Pore kg/hr | Total kg/hr |
|---|---|---|---|
| Water | 20.3 | 5.3 | 25.6 |
| Carbon Monoxide | 0.0 | 0.0 | 0.0 |
| Carbon Dioxide | 47.2 | 12.4 | 59.6 |
| Oxygen | 3.2 | 0.8 | 4.0 |
| Nitrogen | 151.6 | 39.7 | 191.2 |
| Total | 222.2 | 58.2 | 280.4 |

TABLE 2

ENTRAINED REGENERATOR GASES - WITH 75% STRIPPING OF INTERSTITIAL AND PORE CONTAINED VAPOR

|  | Interstitial kg/hr | Pore kg/hr | Total kg/hr |
|---|---|---|---|
| Water | 109.2 | 28.6 | 137.8 |
| Carbon Monoxide | 0.0 | 0.0 | 0.0 |
| Carbon Dioxide | 11.8 | 3.1 | 14.9 |
| Oxygen | 0.8 | 0.2 | 1.0 |
| Nitrogen | 37.9 | 9.9 | 47.8 |
| Total | 159.7 | 41.8 | 201.5 |

Example 2

The experiments described herein were performed using a microflow reactor made of 0.25 inch silicon-steel tubing. A mixture of 95 milligrams (mg) formulated catalyst and 1 gram (g) of 100 micrometer (μm) silicon-carbide was prepared. The mixture was loaded into the reactor, and the reactor temperature increased to 475° C. under helium flow at a rate of 45 milliliters per minute (ml/min) for 30 to 40 minutes. Methanol was flowed through the reactor at a rate of 80 microliters per minute (μl/min) at 475° C., 25 psig (172 kpag) and 100 WHSV (based on the weight of the sieve). The reactor effluent was sampled in a multi-loop sampling valve to obtain the gas phase selectivity data. The collected effluent samples were analyzed by on-line gas chromatography (Hewlett-Packard 6890) equipped with a flame ionization detector, and a Q-column chromatographic column.

The weighed average yields were calculated by taking the weight of the particular hydrocarbon species and dividing by the total effluent less the weights of water, methanol, and dimethylether (DME) in the effluent.

The effect of co-feeding 2 ml/min of air during the oxygenates-to-olefins reaction is shown in Table 3. The partial pressure of oxygen in the feed is 0.36 psia (2.48 kpaa) volume of the methanol feed. The reaction was performed at 100 WSV, 475° C. and a total pressure of 40 psia (276 kpaa) control experiment was performed under identical conditions except that the 2 ml/min air was replaced with 2 ml/min helium.

TABLE 3

| Feed | $C_1$ wt % | $C_2^-$ wt % | $C_{2^o}$ wt % | $C_3^-$ wt % | $C_{3^o}$ wt % | $C_4S$ wt % | $C_5 + S$ wt % | Coke wt % | $C_{2+3}^-$ wt % | Lifetime g/g sieve |
|---|---|---|---|---|---|---|---|---|---|---|
| Air co-feed | 1.65 | 35.45 | 0.26 | 38.25 | 0.69 | 11.47 | 8.90 | 3.34 | 73.70 | 15.81 |
| He co-feed | 1.48 | 35.45 | 0.27 | 39.46 | 0.65 | 13.66 | 6.85 | 2.19 | 74.66 | 24.38 |

$C_1$ → methane
$C_2^-$ → ethlyene

TABLE 3-continued

| | | |
|---|---|---|
| $C_2°$ | → | ethane |
| $C_3^=$ | → | propene |
| $C_3°$ | → | propane |
| $C_4S$ | → | butenes |
| $C_5 + S$ | → | hydrocarbons containing 5 or more carbon atoms |
| $C_{2+3}^=$ | → | ethylene and propene |

The data show that with molecular oxygen in the feed, the catalyst lifetime and prime olefins selectively decreased 35% and 1.3% respectively. The coke selectivity with molecular oxygen in the feed increased 53%.

We claim:

1. A process for converting an oxygenate feedstock into an olefin product stream comprising:
   a) contacting an oxygenate feedstock with a molecular sieve catalyst in a reactor under conditions effective to convert the feedstock into an olefin product stream and to form carbonaceous deposits on the catalyst;
   b) contacting at least a portion of said catalyst having said carbonaceous deposits with an oxygen containing gas under conditions effective to obtain a regenerated catalyst having a reduced carbonaceous deposit level and having an increased molecular oxygen content;
   c) removing at least 60% by volume of said molecular oxygen from said regenerated catalyst based upon the total volume of said molecular oxygen;
   d) returning said regenerated catalyst to said reactor; and
   e) repeating steps (a)–(d).

2. The process of claim 1, further comprising the step of stripping hydrocarbons from said catalyst prior to said step of regenerating said catalyst.

3. The process of claim 2, wherein said stripped hydrocarbons are returned to said reactor.

4. The process of claim 1, wherein at least 65% by volume of said molecular oxygen is removed from said regenerated catalyst based upon the total volume of said molecular oxygen.

5. The process of claim 1, wherein at least 70% by volume of said molecular oxygen is removed from said regenerated catalyst based upon the total volume of said molecular oxygen.

6. The process of claim 1, wherein at least 75% by volume of said molecular oxygen is removed from said regenerated catalyst based upon the total volume of said molecular oxygen.

7. The process of claim 1, wherein at least 80% by volume of said molecular oxygen is removed from said regenerated catalyst based upon the total volume said molecular oxygen.

8. The process of claim 1, wherein between 60% to 95% by volume of said molecular oxygen is removed from said regenerated catalyst based upon the total volume of said molecular oxygen.

9. The process of claim 1, wherein between 65% to 95% by volume of said molecular oxygen is removed from said regenerated catalyst based upon the total volume of said molecular oxygen.

10. The process of claim 1, wherein between 70% to 95% by volume of said molecular oxygen is removed from said regenerated catalyst based upon the total volume of said molecular oxygen.

11. The process of claim 1, wherein between 75% to 95% by volume of said molecular oxygen is removed from said regenerated catalyst based upon the total volume of said molecular oxygen.

12. The process of claim 1, wherein between 80% to 95% by volume of said molecular oxygen is removed from said regenerated catalyst based upon the total volume of said molecular oxygen.

13. The process of claim 1, wherein the oxygenate feedstock is contacted with said molecular sieve catalyst in a riser reactor.

14. The process of claim 1, wherein the oxygenate feedstock comprises at least one of methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

15. The process of claim 1, wherein the oxygenate feedstock is contacted with the molecular sieve catalyst at a temperature in the range of 200° C. to about 700° C.

16. The process of claim 1, wherein the oxygenate feedstock is contacted with the molecular sieve catalyst at a pressure in the range of 0.1 kPa to 100 MPa.

17. The process of claim 1, wherein the oxygenate feedstock is mixed with a diluent comprising at least one of helium, argon, nitrogen, carbon monoxide, carbon dioxide, water, paraffins, aromatic compounds, and mixtures thereof.

18. The process of claim 1, wherein the olefin product stream comprises at least one of ethylene, propylene, butylene and mixtures thereof.

* * * * *